US006823202B2

(12) United States Patent
Hause, Jr.

(10) Patent No.: US 6,823,202 B2
(45) Date of Patent: Nov. 23, 2004

(54) IONTOPHORETIC POWER SUPPLY

(75) Inventor: Robert F. Hause, Jr., Bountiful, UT (US)

(73) Assignee: Iomed, Inc., Salt Lake City, UT (US)

( * ) Notice: Subject to any disclaimer, the term of this patent is extended or adjusted under 35 U.S.C. 154(b) by 267 days.

(21) Appl. No.: 10/113,955

(22) Filed: Apr. 1, 2002

(65) Prior Publication Data
US 2003/0185023 A1 Oct. 2, 2003

(51) Int. Cl.$^7$ ............................................. A61B 5/05
(52) U.S. Cl. ........................ 600/347; 600/309; 600/354
(58) Field of Search ................................ 600/347, 309, 600/345, 354, 355, 372, 382; 604/20

(56) References Cited

U.S. PATENT DOCUMENTS

| | | | | |
|---|---|---|---|---|
| 4,256,978 A | * | 3/1981 | Pinckaers | 327/434 |
| 4,340,047 A | * | 7/1982 | Tapper et al. | 604/20 |
| 4,942,883 A | * | 7/1990 | Newman | 607/152 |
| 5,013,293 A | * | 5/1991 | Sibalis | 604/20 |
| 5,042,975 A | * | 8/1991 | Chien et al. | 604/20 |
| 5,047,007 A | * | 9/1991 | McNichols et al. | 604/20 |
| 5,771,890 A | * | 6/1998 | Tamada | 600/347 |
| 6,223,076 B1 | * | 4/2001 | Tapper | 604/20 |
| 6,687,522 B2 | * | 2/2004 | Tamada | 600/347 |

FOREIGN PATENT DOCUMENTS

| | | |
|---|---|---|
| EP | 1 016 433 A1 | 7/2000 |
| WO | WO 86/07269 | 12/1986 |
| WO | WO 88/08729 | 11/1988 |

* cited by examiner

Primary Examiner—Bao Q. Vu
(74) Attorney, Agent, or Firm—Factor & Lake

(57) ABSTRACT

An iontophoretic power supply comprising hardware and software. The hardware includes means for interfacing with an iontophoretic output device; microprocessor means and a computer readable medium. The software is recorded on the computer readable medium and executable by the microprocessor means. The software is capable of performing the steps of facilitating the providing of at least one operating parameter by a user and applying the provided operating parameters to an interfaced iontophoretic device.

14 Claims, 3 Drawing Sheets

| | | RAMP-UP | | RAMP-DOWN | | DOSE(MA-MIN) | | | SAMPLING | | % |
|---|---|---|---|---|---|---|---|---|---|---|---|
| | MA | MA/SEC | SEC | MA/SEC | SEC | SET | ACTUAL | MIN. | SEC. | NOS. | RAM |
| 01 | +3.00 | 0.100 | 30.0 | 0.200 | 15.0 | 180.0 | 180.4 | 60.5 | 15.0 | 1494 | 1.2 |
| 02 | -4.00 | 0.800 | 5.0 | 0.800 | 5.0 | 1.0 | 1.2 | 0.4 | 15.0 | 48 | 0.0 |
| 03 | +1.00 | 0.030 | 33.8 | 0.100 | 10.0 | 120.0 | 120.1 | 120.4 | 15.0 | 2928 | 2.3 |
| 04 | +0.00 | < ZERO CURRENT WAIT: 3600 SEC> | | | | | | 60.0 | 60.0 | 402 | 0.3 |
| 05 | --OFF-- | | | | | | | | | | |
| 06 | --OFF-- | | | | | | | | | | |
| .. | | | | | | | | | | | |
| .. | | | | | | | | | | | |
| 15 | --OFF-- | | | | | | | | | | |
| 16 | --OFF-- | | | | | | | | | | |
| TOTAL PER SEQUENCE | | | | | | 301.0 | 301.6 | 241.3 | | 4872 | 3.8 |
| TOTAL 2 SEQUENCE (S) | | | | | | 602.0 | 603.2 | 482.6 | | 9744 | 7.6 |
| VOLTAGE LIMIT-30.0 VOLTS | | | | | | | | | | | |

Fig 2

| MA | RAMP-UP MA/SEC | SEC | RAMP-DOWN MA/SEC | SEC | DOSE (MA-MIN) SET | ACTUAL | MIN. | SAMPLING SEC. | NOS. | % RAM |
|---|---|---|---|---|---|---|---|---|---|---|
| 01 | +4.00 | 0.133 | 30.0 | 0.267 | 15.0 | 80.0 | 80.5 | 20.5 | 5.0 | 1518 | 1.2 |
| 02 | --OFF-- | | | | | | | | | | |
| .. | | | | | | | | | | | |
| .. | | | | | | | | | | | |
| 15 | --OFF-- | | | | | | | | | | |
| 16 | --OFF-- | | | | | | | | | | |
| TOTAL PER SEQUENCE | | | | | 80.0 | 80.5 | 20.5 | | 1518 | 1.2 |
| TOTAL 1 SEQUENCE(S) | | | | | 80.0 | 80.5 | 20.5 | | 1518 | 1.2 |

VOLTAGE LIMIT = 70.0 VOLTS

Fig 6

```
DLP S/N 000-000-013
MANUFACTURED ON 4 MAY 2001
CALIBRATED BY R.F.H. ON 15 JUNE 2001
DLP CORRECTION CONSTANTS:
   -2.0 % FOR ANO VMEAS1    (VOLTS)
   -1.6 % FOR AN1 VMEAS2    (VOLTS)
    0.3 % FOR AN4 CURRENT   (MAMPS)
    2.7 % FOR AN5 BATTERY   (VOLTS)
    0.4 % FOR AN6 USER1     (VOLTS)
   -0.0 % FOR AN7 USER2     (VOLTS)

FIRST CYCLE STARTED
FRIDAY 27 JULY 2001 AT 9:04:43
ID: 000657 TOTAL SEQUENCES: 1, TOTAL CYCLES: 1, VOLTAGE LIMIT: 69.9
SEQUENCE: 1 OF 1, CYCLE: 1 OF 1
CURRENT: 4.000 MA, DOSE: 80.0 MA-MIN
SAMPLE RATE: 5:00 SECONDS
RAMPUP: 0.133 MA/SEC, RAMPDOWN: 0.267 MA/SEC
AN6: 4.986, AN7: 0.008, BATTERY: 8.016
00001,   0.008,    0.160,    0.160,    0.000
00002,   0.008,    0.160,    0.160,    0.000
00003,   0.008,    0.160,    0.160,    0.000
00004,   0.008,    0.160,    0.160,    0.000
00005,   0.006,   13.230,    8.110,    5.120
 ..
00271,   4.009,   17.800,    8.260,    9.000
00272,   4.006,   17.770,    8.270,    9.500
DOSE COMPLETE
FRIDAY 27 JULY 2001 AT 9:25:23
AN6: 4.986, AN7: 0.008, BATTERY: 7.772
00273,   3.447,   16.390,    7.830,    8.560
00274,   2.104,   13.350,    7.740,    5.610
00275,   0.779,   10.370,    8.160,    2.210
LAST CYCLE COMPLETE
FRIDAY 27 JULY 2001 AT 9:25:40
AN6: 4.986, AN7: 0.008, BATTERY: 7.856
00276,   0.000,    0.150,    0.160,   -0.010
TRANSPORT SHUTDOWN
FRIDAY 27 JULY 2001 AT 9:25:48
```

IONTOPHORETIC POWER SUPPLY

BACKGROUND OF THE INVENTION

1. Field of the Invention

The invention relates in general to an iontophoretic power supply, and, more particularly to an iontophoretic power supply that includes many parameters which are user programmable and which is capable of recording data pertaining to the supply of electrical current, voltage, and power, therefrom.

2. Background Art

Iontophoretic power supplies have been known in the art. Such power supplies are used to provide the necessary electrical force to transfer ions across a medium. Generally, such systems are associated with a primary electrode, a return electrode and a pharmaceutical component which is placed into the primary electrode. The technology is based on the principle that an electrical potential will cause ions in solution to migrate according to their electrical charge.

There are basically three different types of iontophoretic power supplies, namely (1) the miniature integrated iontophoretic power supply, (2) the portable iontophoretic power supply and (3) the benchtop laboratory iontophoretic power supply. Each of these power supplies is configured for operation in association with a particular iontophoretic electrode assembly device and at particular operating parameters.—Currently it is both time consuming and expensive to design, assemble, test, and validate new types of iontophoretic power supplies, be it for research devices, prototypes, or new product development. Typically the time required is measured in months.

As such, it would be an object of the invention to provide a power supply, which includes a plurality of user definable and settable parameters, to, in turn, emulate a plurality of different power supplies. This power supply can be reconfigured, tested, and validated, for example to provide a new functional prototype, within one hour's time. This provides an invaluable tool for scientific researchers conducting iontophoretic experiments, because such researchers cannot effort the time required to develop a new iontophoretic power supply, nor may they have personnel required to design or modify power supplies. This also provides an invaluable tool for the engineers and technicians responsible for prototyping new iontophoretic power supplies.

It is another object of the invention to provide a power supply that is capable of periodically collecting data pertaining to operating parameters that can then be transferred to a computer for analysis.

These and other objects will become apparent in light of the specification and claims appended hereto.

SUMMARY OF THE INVENTION

The invention comprises an iontophoretic power supply. The power supply includes both hardware and software. The hardware includes means for interfacing with an external output device, means for interfacing with an external communication device, means for interfacing with sensors, microprocessor means and a computer readable medium. The term "microprocessing", used herein, still imply electronic state machine processing. The microprocessing means may be facilitated with a microprocessor, microcontroller, FPGA, ASIC, or the like. The term "software", used herein, shall mean programmed machine code instructions, be it soft code, firm code, or the like. The software is recorded on the computer readable medium and executable by the microprocessor means. The software is capable of performing the steps of facilitating the providing of at least one operating parameter by a user; and applying the provided operating parameters to an interfaced iontophoretic electrode assembly device.

In a preferred embodiment of the invention, the iontophoretic electrode assembly device (or external output device) interfacing means comprises a pair of leads which are associatable with opposing electrodes (i.e., anode and cathode) of an iontophoretic electrode assembly device.

In another preferred embodiment of the invention, the at least one operating parameter comprises at least one parameter selected from the group consisting of: voltage limit, steady state current magnitude, current polarity, ramp-up rate, ramp-down rate, number of cycles and number of sequences.

In another preferred embodiment of the invention, the software further performs the step of storing data gathered during the step of applying the provided operating parameters to the external output device. In one such preferred embodiment of the invention, the hardware further includes means for communicating with an external communication device. In turn, the software further performs the step of transmitting the stored data gathered during the step of applying the provided parameters to an external communication device.

In another such preferred embodiment of the invention, the hardware further includes at least one sensor. The software further performs the step of storing data pertaining to the sensor during the step of applying the provided operating parameters to the external communication device.

In a preferred embodiment of the invention, the hardware further includes means for communicating with an external communication device. In such an embodiment, the step of facilitating the entry of at least one operating parameter by a user further comprises the step of transferring at least one operating parameter from an external communication device to the power supply through the communicating means.

In a preferred embodiment of the invention, the at least one operating parameter comprises a plurality of operating parameters.

The invention further comprises a method of emulating an iontophoretic power supply to supply an iontophoretic treatment via an iontophoretic electrode assembly device. The method comprising the steps of providing at least one operating parameter to the power supply, and, applying the provided operating parameters to the iontophoretic electrode assembly device to execute a treatment.

In a preferred embodiment of the invention, the step of providing further comprises at least one of the steps of providing a voltage limit, providing a steady state current magnitude, providing a current polarity, then providing a current ramp-up rate, then a current ramp-down rate, providing a number of cycles, and providing a number of sequences.

In another preferred embodiment of the invention, the step of providing further comprises the step of communicating with an external communication device and receiving at least one operating parameter from the external communication device.

In yet another preferred embodiment of the invention, the method further comprises the step of providing data pertaining to the treatment to a user via a display associated with the power supply.

In yet another preferred embodiment of the invention, the method further comprises the step of storing data pertaining to the treatment. In one such embodiment, the method further comprises the steps of communicating with an external communication device and transferring stored data to the external communication device.

Preferably, the method includes the steps of associating at least one sensor to the power supply and storing data pertaining to the at least one sensor. In one such embodiment, the method further includes the steps of communicating with an external communication device and transferring stored data pertaining to the at least one sensor to the external communication device.

BRIEF DESCRIPTION OF THE DRAWINGS

Reference will be made to drawings appended hereto in which:

FIG. 2 of the drawings is a sample display of a particular exemplary setting of the operating parameters of the power supply of FIG. 1;

FIG. 6 of the drawings is a sample display of the data obtained and stored in the data storage means for later analysis and review.

BEST MODE FOR PRACTICING THE INVENTION

Figures 1, 4:
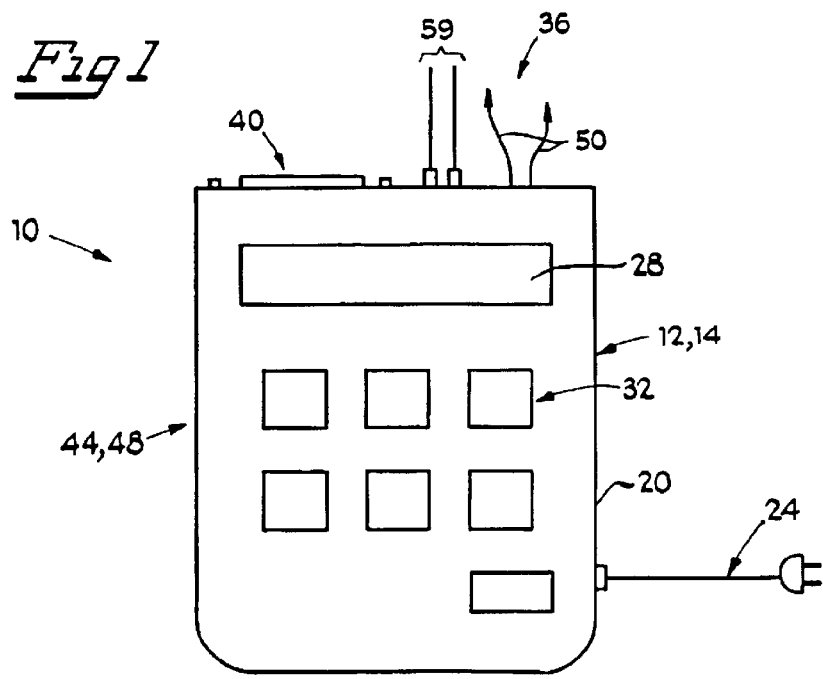
FIG. 1 of the drawings is a perspective view of a power supply of the present invention.
FIG. 4 of the drawings is a sample display of another particular exemplary setting of the operating parameters of the power supply of FIG. 1.

While this invention is susceptible of embodiment in many different forms, there is shown in the drawings and will be described in detail, one specific embodiment with the understanding that the present disclosure is to be considered as an exemplification of the principles of the invention and is not intended to limit the invention to the embodiment illustrated.

Referring now to the Figures, and in particular, to FIG. 1 of the drawings, reconfigurable data logging iontophoretic power supply (hereinafter the power supply) is shown generally at 10. Power supply 10 is shown as comprising hardware 12 and software 14 which operates on hardware 12. The power supply is contemplated for use in association with a variety of different types of iontophoretic electrode assembly devices. It will be understood that the power supply 10 can likewise be used in association with controlled bodily analyte extraction as well as other various uses.

Hardware 12, as shown in FIG. 1, includes housing 20, power supply 24, means 28 for displaying information to a user, means 32 for providing input by a user; means 36 for interfacing with an external output device, means 40 for providing outside communication; microprocessing means 44 and storage means 48 (i.e., a computer readable medium). While various different types of hardware are contemplated for use, including, but not limited to, personal computers, personal digital assistants, the embodiment disclosed comprises a specially configured single purpose device.

Housing 20 which sized and shaped so as to retain the necessary componentry, while facilitating easy handling and storage for a user. Power supply 24 may comprise a variety of power supplies capable of providing the necessary range of voltages and currents that may be selected by an operator. For example, the power supply may comprise a medical grade isolated AC line powered adapter that is suitable for medical uses. In other embodiments, batteries (such as AA, C, D, among others) can be utilized to provide an additional portability to the device. The batteries may be internal or external to the housing 20. In such embodiments, the device may include a low battery warning to indicate that the batteries require replacement. It is contemplated that the batteries may comprise secondary batteries that can be charged by an AC line powered adapter.

Display means 28 is shown in FIG. 1 as comprising a LCD with two rows of 16 characters. Such a display provides the necessary information while minimizing the cost associated with displays and the power consumption of displays. The information provided can include the instantaneous or average operating parameters. Of course, the display can be configured to provide other information as well. In other embodiments, a display can be provided which includes greater size (4 line, QVGA, 160×160, etc) and greater resolution (2 bit gray scale, 4 bit gray scale, 8 bit color, 16 bit color, etc) which can provide more information to a user through the display.

User input means 32 is shown in FIG. 1 as comprising a plurality of touch sensitive push buttons on the top surface of the display. Certain of the touch sensitive pushbuttons comprise single purpose pushbuttons, and other of the touch sensitive pushbuttons comprises multi-purpose push buttons. In this manner, the total quantity of push buttons that are required can be minimized. It will be understood that in certain embodiments, the touch sensitive push buttons can be replaced with keyboard push-buttons (i.e., a conventional keyboard), or by "software" push buttons displayed on a touch-sensitive display, a series of switches, etc. Indeed, various types of user input means are contemplated for use which provide the user with the ability to direct the power supply to execute a desired function.

External output device interfacing means 36 is shown in FIG. 1 as comprising a set of leads 50 which are associatable with the respective anode and cathode of an iontophoretic electrode assembly device. Such leads 50 may comprise some type of jack, such as a conventional two pole jack. In other embodiments, the leads may comprise terminals, a pair of alligator clips, etc. Regardless of the embodiment, leads 50 provide for connection between the power supply and an outside iontophoretic electrode assembly device. In other embodiments additional device interfacing means 38 may be provided to, for example, interface with various sensors via sensor leads 59. This could include the following types of sensors: temperature, humidity, skin pH, interfacial voltage potentials, etc. These additional sensors can provide data relative to various different parameters during the execution of a treatment.

Outside communication means 40 is shown in FIG. 1 as comprising a data port, which can be configured to couple with, for example, a personal computer. In the embodiment shown in FIG. 1, the data port comprises an isolated RS232 serial port. In other embodiments, the data port may comprise a parallel port, a USB port, wired or wireless 802.11 communication, Bluetooth communication, IRDA, among others. Indeed, in certain embodiments, the outside communication means may comprise a plurality of ports to facilitate association with a plurality of different devices. As will be explained, the outside communication means facilitates the transfer of data from an outside device to, in turn, transfer operating parameters to the power supply. In addition, the outside communication means facilitates the transfer of data to the external communication device to, in turn, transfer stored data pertaining to sensors or a treatment from the data storage means of the power supply.

Microprocessing means 44 may comprise a microprocessor or microcontroller or custom ASIC or similar integrated circuit controller and associated circuitry capable of being operated by software 14 to perform a treatment according to the selected operating parameters and to facilitate and coordinate the transfer and processing of data. The particular design of the microprocessing means can be varied and can be determined by one of skill in the art having the present disclosure. In addition, storage means 48 is associated with the microprocessing means and is capable of storing various data at the direction of the microprocessing means. Storage means 48 is likewise capable of interfacing with outside communication means 40 so as to facilitate the transfer of data from the storage means to an external communication device. The storage means may comprise computer readable medium including, but not limited to, RAM; flash memory such as SC, MMC, SM, CF and MS; magnetic disc media such as a hard drive or a floppy drive; an optical drive CD-R, CD-RW, DVD-RAM; among others.

It will be understood that software 14 is provided so as to provide the desired functionality to the device and the desired output to an external output device (e.g., iontophoretic electrode assembly device) which is connected to external output device interfacing means 36 by way of leads 50. Software 14 can be stored on the data storage means, or may be stored on another computer readable medium or may be firmware. Software 14, can direct the power supply to vary the following parameters: voltage limit, steady state current magnitude, current polarity, ramp-up rate, ramp-down rate, number of cycles, number of sequences, etc. In addition, software 14 can direct the storage means to store data which relates to the performance of the external device when presented with the different output from the power supply. In turn, software 14 can control the operation of hardware 12 such that a single power supply of the present invention can be utilized to emulate an infinite number of different power supplies having a plurality of different operating parameters, and the device can store the performance of the device in response to the different operating parameters.

To provide for a treatment, the user can input the desired parameters into the device via the input means 32. Alternatively, the user can program the desired parameters in a personal computer or other external communication device and then transfer the desired parameters to the power supply via the outside communication means 40. The user can program any one of a number of different programs and sequences, and is not limited to any particular set of parameters.

For example, a set of parameters can be programmed to emulate a conventionally available power supply, such as a PM850 Phoresor available from IOMED, INC. of Salt Lake City, Utah. A typical printout of the configured parameters is shown in FIG. 2. Such parameters comprise a single sequence, single cycle treatment for an 80 milliamp-minute drug delivery treatment utilizing a steady state current of 4.0 milliAmps. Such a treatment is commonly utilized with state-of-the-art hand-held drug delivery iontophoretic power supplies, in conjunction with dexamethasone sodium phosphate, for the site-specific non-invasive treatment of local inflammation. The parameters further include a ramp-up rate of 0.133 milliAmps per second and a ramp-down rate of 0.267 milliAmps per second. The parameters further prescribe a voltage limit of 70.0 Volts. The user can additionally specify a desired sampling rate at which data is collected by the data storage means. In the example shown in FIG. 2, iontophoretic current and total device output voltage is sampled and stored every 5.0 seconds. It will be understood that due to the infinite variability, the user could alter any one of the parameters as desired.

Figure 3:
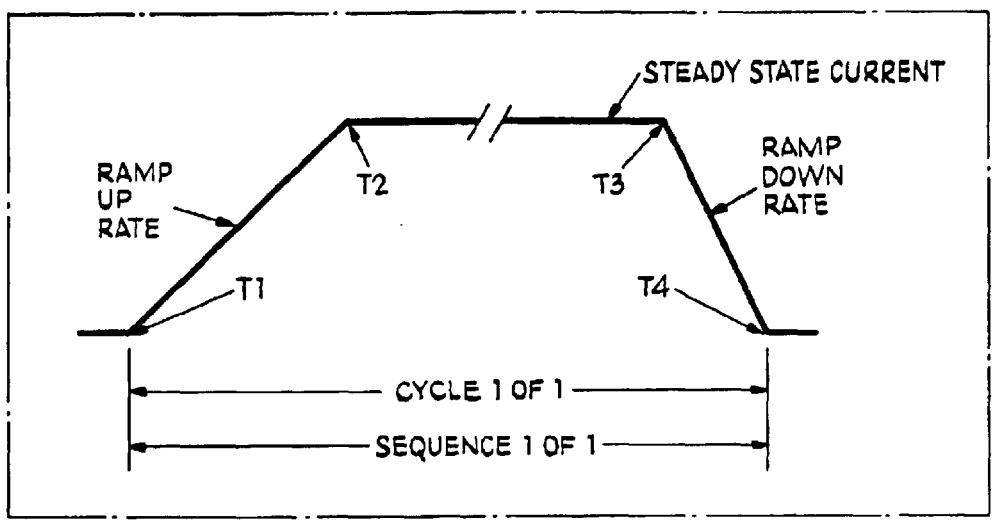
FIG. 3 of the drawings is a graphical representation of the operation of the power supply utilizing the parameters identified in FIG. 2.

A graphical representation of the treatment for the parameters of FIG. 2 is shown in FIG. 3. In particular, at time T1 the current ramp-up is initiated. At time T2 the ramp-up is completed. Once the current ramp-up is completed, the current will remain at the steady state value of 4.0 milliAmps until T3, at which time the dose of 80.0 milliAmp-minutes has been achieved. Based on the configuration of the parameters given in FIG. 2, T3 is reached 20.5 minutes after T1. Lastly, the current is ramped-down and reaches zero at T4.

Figure 5:
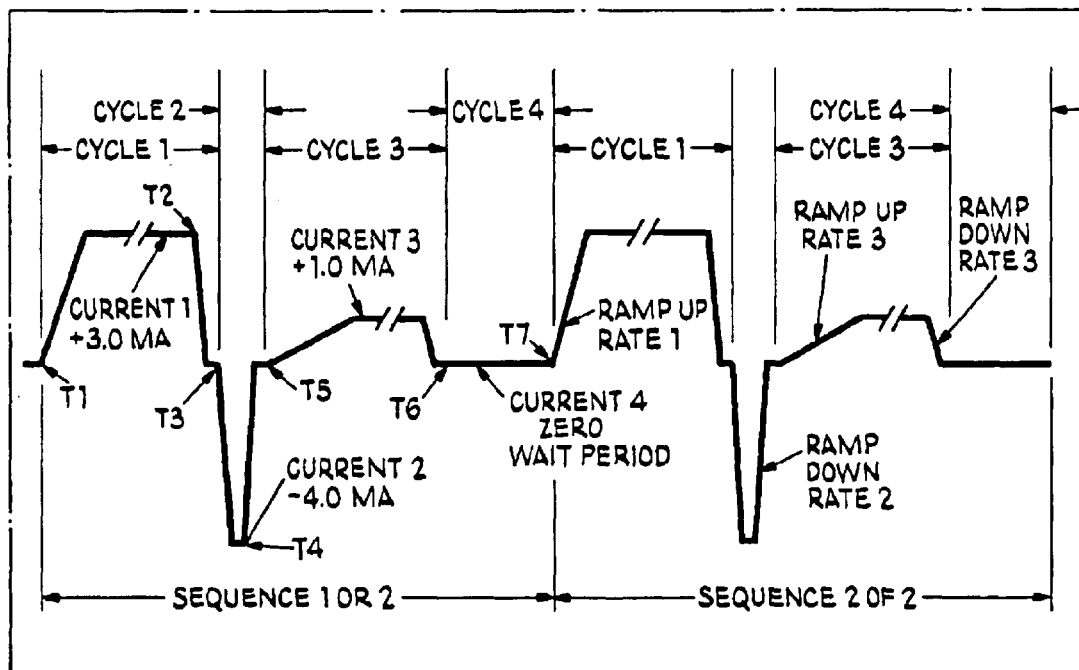
FIG. 5 of the drawings is a graphical representation of the operation of the power supply utilizing the parameters identified in FIG. 4.

In another example, a multiple-cycle and multiple sequence treatment is shown. In particular, such a treatment could be utilized with a medium voltage miniature integrated iontophoretic power supply that is used for postoperative analgesic drug delivery systems. A typical parameter configuration print out is shown in FIG. 4. In such an example, the parameters prescribe four cycles and two sequences of the four cycles. It will be understood that the system is not limited to any particular number of cycles and sequences, such limitations are generally a function of the memory capacity of the data storage means and the programming of the software. For example, each cycle of the four cycles is provided with a unique current magnitude, current polarity, ramp-up rate, ramp-down rate, dose and sampling rate. In the example described, the parameters set the voltage limitation to 30 volts. With respect to data storage, the sampling rate has been set to 15.0 seconds for the first three cycles and 60.0 seconds for the final cycle. A graphical representation of the treatment is shown in FIG. 5. Again, and as can be seen from the foregoing examples, a plurality of different parameters can be set by the user prior to treatment and the system is not limited to any particular set of parameters and particular set of values for such parameters.

As identified above, the power supply software is likewise capable of monitoring certain aspects of the operation and storing data gathered during the operation of the device. Such data may be gathered from internal sensors, which for example include the iontophoretic current and the iontophoretic voltage at any given time in a cycle. Additional external sensors may be utilized. For example voltage probes may be inserted at various points in the iontophoretic circuit, to, in turn, provide data pertaining to voltage drops or resistances along certain paths of the iontophoretic circuit. For another example the following types of sensors could be utilized: humidity, temperature, skin pH, etc. The data, collected from these internal sensors or external sensors, is stored by the data storage means and can then be transmitted by outside communication means 40 to a personal computer for analysis. Such analysis is invaluable when [1] designing and implementing an iontophoretic device and/or an iontophoretic power supply, or [2] when conducting general iontophoretic research. A typical display of the data stored by the power supply is shown in FIG. 6.

It will be understood that the foregoing device can provide invaluable assistance with the development and testing of iontophoretic power supplies. The time to plan, implement, assemble, test, verify and validate a new iontophoretic power supply can measure in years. The time necessary to modify an existing power supply, for example to generate a new prototype or research-specific device, can take weeks or months. To the contrary, different parameters can be varied and tested quickly by the power supply of the present invention to determine the viability of a particular design, and, modifications can be attempted immediately by altering the variable parameters of the power supply of the present invention. In addition, data pertaining to the operation of the power supply with the given parameters can be stored and analyzed.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. An iontophoretic power supply comprising:
   hardware including
      means for interfacing with an external output device;
      means for interfacing with an external communication device;
      means for interfacing with sensors;
      microprocessor means; and
      computer readable medium; and;
   software, recorded on the computer readable medium, executable by the microprocessor means, for performing the steps of:
   facilitating the providing of at least one operating parameter by a user, the at least one operating parameter comprising at least one parameter selected from the group consisting of: voltage limit, steady state current magnitude, ramp-up rate, ramp-down rate, number of cycles and number of sequences; and
   applying the provided operating parameters to an interfaced iontophoretic device.

2. The iontophoretic power supply of claim 1 wherein the external output device interfacing means comprises a pair of leads which are associatable with opposing electrodes of an iontophoretic device.

3. The iontophoretic power supply of claim 1 wherein the software further performs the step of: storing data gathered during the step of applying the provided operating parameters to the external output device.

4. The iontophoretic power supply of claim 3 wherein the hardware further includes means for communicating with an external device, the software further performing the step of transmitting the stored data gathered during the step of applying the provided parameters to an external output device.

5. The iontophoretic power supply of claim 3 wherein the hardware further includes at least one sensor, be it internal or external, the software further performing the step of storing data pertaining to the sensor during the step of applying the provided operating parameters to the external output device.

6. The iontophoretic power supply of claim 1 wherein the hardware further includes means for communicating with an external device, the step of facilitating the entry of at least one operating parameter by a user further comprises the step of: transferring at least one operating parameter from an external device to the power supply through the communicating means.

7. The iontophoretic power supply of claim 1 wherein the at least one operating parameter comprises a plurality of operating parameters.

8. A method of emulating an iontophoretic power supply to supply an iontophoretic treatment via an iontophoretic device, the method comprising the steps of:
   providing at least one operating parameter to the power supply, the operating parameter comprising at least one parameter selected from the group consisting of voltage limit, steady state current magnitude, ramp-up rate, ramp-down rate, number of cycles and number of sequences; and
   applying the provided operating parameters to the external iontophoretic device 9. The method of claim 8 wherein the step of providing further comprises the step of:
   communicating with an external device; and
   receiving at least one operating parameter from the external device.

10. The method of claim 8 further comprising the step of:
    providing data pertaining to the treatment to a user via a display associated with the power supply.

11. The method of claim 8 further comprising the step of:
    storing data pertaining to the treatment.

12. The method of claim 11 further comprising the step of:
    communicating with an external device;
    transferring stored data to the external device.

13. The method of claim 11 further comprising the step of:
    associating at least one sensor to the power supply; and
    storing data pertaining to the at least one sensor.

14. The method of claim 13 further comprising the step of:
    communicating with an external device; and
    transferring stored data pertaining to the at least one sensor to the external device.

* * * * *